United States Patent [19]

Suzuki et al.

[11] 4,292,299

[45] Sep. 29, 1981

[54] SLOW-RELEASING MEDICAL PREPARATION TO BE ADMINISTERED BY ADHERING TO A WET MUCOUS SURFACE

[75] Inventors: Yoshiki Suzuki; Hiroshi Ikura, both of Hino; Gentaro Yamashita, Koganei, all of Japan

[73] Assignee: Teijin Limited, Osaka, Japan

[21] Appl. No.: 202,384

[22] PCT Filed: Nov. 6, 1979

[86] PCT No.: PCT JP79/00284

§ 371 Date: Jul. 7, 1980

§ 102(e) Date: Jul. 7, 1980

[87] PCT Pub. No.: WO80/00916

PCT Pub. Date: May 15, 1980

[30] Foreign Application Priority Data

Nov. 6, 1978 [JP] Japan ................. 53-135883

[51] Int. Cl.³ .................. A61L 15/03; A61K 9/24
[52] U.S. Cl. .................... 424/16; 128/156; 128/260; 128/268; 424/19; 424/21; 424/28
[58] Field of Search ............ 128/156, 260, 268; 424/14, 16, 19–22, 28

[56] References Cited

U.S. PATENT DOCUMENTS

| | | | |
|---|---|---|---|
| 3,249,109 | 5/1966 | Maeth et al. | 128/268 |
| 3,339,546 | 9/1967 | Chen | 128/268 |
| 3,444,858 | 5/1969 | Russell | 128/260 |
| 3,536,809 | 10/1970 | Applezweig | 424/28 |
| 3,696,811 | 10/1972 | Chen | 128/156 |
| 3,911,099 | 10/1975 | Defoney et al. | 424/28 |
| 3,972,995 | 8/1976 | Tsuk et al. | 424/28 |
| 4,039,653 | 8/1977 | Defoney et al. | 424/19 |
| 4,059,686 | 11/1977 | Tanaka et al. | 424/22 |
| 4,226,848 | 10/1980 | Nagai et al | 424/19 |
| 4,250,163 | 2/1981 | Nagai et al. | 424/14 |

FOREIGN PATENT DOCUMENTS

| | | |
|---|---|---|
| 2908847 | 11/1980 | Fed. Rep. of Germany . |
| 2450618 | 3/1980 | France . |
| 51-38412 | 3/1976 | Japan . |
| 53-86011 | 7/1978 | Japan . |
| 53-130421 | 11/1978 | Japan . |
| 54-38168 | 11/1979 | Japan . |
| 55-62012 | 10/1980 | Japan . |

OTHER PUBLICATIONS

Teijen, Ltd. WO 80/00916 (15.05.80) PCT/JP79/00284 (25 pp.), Sustained-Release Preparation Used in Adhesive Contact with Wet Surface.
Husa's Pharmaceutical Dispensing 5th ed. (1959), Mack Publishing Co., Easton, Pa., pp. 35–36 (Dusting Powders), 62–68, 76–80 (Tablets) 120–122 (Suppositories).

*Primary Examiner*—Shep K. Rose
*Attorney, Agent, or Firm*—Sughrue, Mion, Zinn, Macpeak & Seas

[57] ABSTRACT

A medical preparation composed of an adhesive layer comprising polymers which have adhesiveness to a wet mucous surface and swellability upon moistening and a nonadhesive layer which has no adhesiveness to a wet mucous surface and is water soluble or water disintegrable, with at least one of the layers made to contain a medicament. The medical preparation is administered by adhering to a wet mucous surface of the mucous membrane and skin of men or animals, whereby exhibiting a property to release the medicament slowly extending over a long period of time to cure or prevent general or local diseases.

9 Claims, No Drawings

SLOW-RELEASING MEDICAL PREPARATION TO BE ADMINISTERED BY ADHERING TO A WET MUCOUS SURFACE

TECHNICAL FIELD

The present invention relates to a slow-releasing medical preparation to be administered by adhering to the wet mucous surface of a mucous membrane and skin of men or animals. More particularly, this invention relates to a slow-releasing medical preparation, which has improved handle-ability and adhesiveness, comprising a layer which displays adhesiveness to the wet mucous surface and a layer which has no adhesiveness, at least either one of which layers is made to contain a medicament.

BACKGROUND ART

Several suggestions have hitherto been made as to slow-releasing medical preparations from which a medicament contained therein is made to gradually release to maintain the efficacy of the medicament over a long period of time after they are administered to men or animals by adhering to their mucous membrane.

For instance, Japanese Laid-Open Pat. Publication No. 38412/76 (U.S. Pat. No. 4,059,686, patented Nov. 22, 1977) discloses a buccal preparation which is to be used by adhering to the buccal mucous membrane, being composed of a medicament, a sodium salt of polyacrylate, and an excipient (i.e., crystalline cellulose, mannitol, lactose, sorbitol, anhydrous calcium phosphate, amilose, etc.). Japanese Laid-Open Pat. Publication No. 130421/78 discloses a preparation for treatment of uterine cancer, to be used by adhering to the uterus mucous membrane, comprising hydroxypropyl cellulose, polyacrylic acid or its salt, and a carcinostatic agent.

However, these slow-releasing preparations, when they are prepared in the form of a tablet, they have adhesiveness on both the upper surface and the reverse surface which presents some demerits, for instance, of making the handling inconvenient and often adhering to other place not desired at the time of administration. In order to lessen the touchy discomfort at the place where a slow-releasing preparation is adhered, it is preferable to make the preparation as thin as possible; however, there has been a problem that it is hardly possible to make the thickness of the conventional slow-releasing preparation less than about 1 mm from the viewpoint of mechanical strength.

The present inventors have come to complete this invention after having made a serious study with the object of developing an improved slow-releasing preparation to be used by adhering to the wet surface of mucous membrane, etc. to mend the faults found with the prior arts.

DISCLOSURE OF INVENTION

The present invention relates to a slow-releasing medical preparation to be administered by adhering to the wet mucous surface comprising an adhesive layer composed of a polymer which has the adhesiveness to the wet mucous surface and a property to swell upon moistening and a nonadhesive, either water soluble or disintegrable, layer which has no adhesiveness to the wet mucous surface and at least either one of said adhesive layer and nonadhesive layer is made to contain a medicament.

BEST MODE OF CARRYING OUT THE INVENTION

In the present invention, a slow-releasing preparation which is administered by adhering to the wet mucous surface consists of two layers, an adhesive layer and a nonadhesive layer, speaking from the structural viewpoint. And the adhesive layer is a layer which has the adhesiveness to the wet mucous surface of mucous membrane and skin of men or animals and is composed of a polymer which has adhesiveness to the wet mucous surface and a property to swell upon moistening or a combination of said polymer and a medicament.

The adhesive layer comprises a polymer, which displays adhesiveness towards the wet mucous surface and has a property to swell when moistened, to work as an adhesive component. It is aimed at the administration of the preparation fixed to the mucous membrane of the body cavity such as the oral cacity, etc. and the adhesiveness required for fixing the preparation differs depending upon the place of administration in the body cavity. Generally speaking, comparatively greater adhesiveness is required for the place like an oral cavity where larger quantity of motion is common. On the other hand not so much adhesiveness is required for the place where only a small quantity of motion is usual since the strength required for peeling off the preparation is small in such a place. In most cases, the adhesiveness of more than about 40 g/cm$^2$ adhesion area measured according to a measuring method described later is enough to fix the preparation to the wet mucous surface. When the administration of the preparation by continued fixation is intended for the place where the quantity of motion is especially large, it is desirable to increase the adhesiveness to about 150 g/cm$^2$ adhesion area. The property to swell upon moistening possessed by the polymer used for the adhesive layer, when medicated, is necessary for the gradual release of the medicament, which, however, is also a desirable property for the nonadhesive layer, when medicated.

As polymers to be used for an adhesive layer, for instance, such homopolymer fo acrylic acid monomer as polyacrylic acid, polyacrylic acid sodium salt, polyacrylic acid potassium salt, polyacrylic acid ammonium salt or their pharmaceutically acceptable nontoxic salts; copolymers of acrylic acid obtained by copolymerization of acrylic acid as a main component and methacrylic acid, styrene, or vinyl ethers (methyl vinyl ether, etc.) as a comonomer, or their pharmaceutically acceptable nontoxic salts; such hydrophilic vinyl polymers as polyhydroxyethyl acrylate, polyhydroxyethyl methacrylate, polyvinyl alcohol, polyvinyl pyrrolidone, etc.; such hydrophilic cellulose derivatives as methyl cellulose, hydroxyethyl cellulose, hydroxypropyl cellulose, hydroxypropylmethyl cellulose, carboxymethyl cellulose or their salts; such polysaccharides as hydroxypropyl starch, alginic acid, sodium alginate, and tragacanth gum or their derivatives; and further such derivatives having improved swellability as collagen, gelatine or radiobridged gelatine, chemically modified gelatine (for instance, gelatine denatured by phthalic anhydride or succinic acid) may be mentioned.

These polymers can be used as an adhesive layer either singly or in the form of a mixture of two or more. In addition to a medicament, the adhesive layer may further contain other ingredients, for instance, such as publicly known expipient, binder, disintegrator, coloring agent, corrigent, lubricent, etc., provided that the layer maintains said adhesiveness to the wet mucous surface.

Another of the layers which constitute the slow-releasing preparation of the present invention is a nonadhesive layer which has no adhesiveness to the wet mucous surface (the adhesiveness is less than about 10 g/cm$^2$ adhesion area) and this layer is required to be water soluble and water disintegrable. This layer may be made to contain a medicament.

Water soluble or water disintegrable ingredients which compose the abovementioned nonadhesive layer may be any of ingredients so far as they have such required properties and are pharmaceutically acceptable. Choice may be made of them depending upon the place of administration. As ingredients to compose such a nonadhesive layer, for instance, lactose, glucose, sucrose, starch, crystalline cellulose, dextrin, cyclodextrin, silicic acid anhydride, aluminum silicate, talc, calcium stearate, magnesium stearate, beeswax, polyethylene glycol, polyphosphate, etc. may be mentioned. These materials can be used for preparing a nonadhesive layer singly or in the form of a mixture consisting of two or more. In addition to a medicament, other materials, for instance, such as publicly known excipient, binder, disintegrator, coloring agent, corrigent, lubricant, etc. may be contained in the nonadhesive layer.

In case where the adhesive layer of the slow-releasing preparation is medicated in the present invention, it adheres to the wet mucous surface of a body cavity upon administration and the nonadhesive layer dissolves or disintegrates in the presence of the body cavity secretion to expose the adhesive layer in the body cavity. Then the adhesive layer starts swelling due to the body cavity secretion and, as it swells, it slowly releases the medicament. In case where the nonadhesive layer is made to contain a medicament, when the preparation is adhered to the wet mucous surface of the body cavity, the nonadhesive layer gradually dissolves or disintegrates due to the presence of the body cavity secretion, thus slowly releasing the medicament. In this case, the adhesive layer which contains no medicament remains stuck to the body cavity after the disappearance of the nonadhesive layer or disappearance of the medicament. This adhesive layer, having a property to swell in the presence of water, may gradually disintegrate and disappear, when left stuck to the oral cavity, etc. However, it can be removed with force from where it adheres, if necessary. When it swells up enough, it can be removed easily with the tip of a finger or anything like a spatula. It can be understood from the above fact that the swelling property of the adhesive layer is not only a nature necessary when the adhesive layer is made to contain a medicament but also a nature desirable when the nonadhesive layer is made to contain a medicament.

When a comparison is made between a case where the adhesive layer is made to contain a medicament and a case where the nonadhesive layer is made to contain a medicament, the former has a nature of releasing the medicament much slower than the latter as the above case shows. Therefore, it is advisable to make a choice depending upon the condition of a disease or the nature of a medicament making the best use of such difference of nature. Therefore, utilizing the different natures of the adhesive layer and the nonadhesive layer as mentioned above, both the two layers may be made to contain a medicament alike and the two layers may be made to contain a medicament with a different kind of medicament respectively, thus both cases representing a desirable mode of medical care, as circumstances require.

As it is understood clearly from what mentioned above, in the slow-releasing preparation of the present invention, irrespective of which layer contains a medicament, the nonadhesive layer dissolves or disintegrates to disappear sooner or later after the administration while the adhesive layer remains stuck to the wet mucous surface. A feeling of touchy irritancy caused by the adhering preparation differs in degree depending upon the sensibility of a patient and the place of administration and if the thickness of the adhesive layer is about 2.5 mm or less, the use of the preparation is quite bearable even if there is some feeling of touchy irritancy. If the thickness of an adhesive layer is 0.1 mm or more, the layer can maintain enough slow-releasing property. From this fact it has been made understood that the thickness of the adhesive layer is preferably in the range of approx. 0.1 mm to approx. 2.5 mm, and it is especially preferable to have the thickness of the layer in the range of approx. 0.1 to 1.0 mm. It is preferable to make a selection of thickness of a nonadhesive layer in the range of approx. 0.1 mm to approx. 2.5 mm.

As mentioned above, the slow-releasing preparation of the present invention comprises the two kinds of layer. When the preparation is made of two layers, the nonadhesive layer and the adhesive layer cooperate together to increase each other's efficiency. Thus it has been made possible to make the adhesive layer thinner when compared with conventional slow-releasing preparations which comprise an adhesive layer only. For instance, if the adhesive layer having a thickness of 0.1 to 1.0 mm has a problem in terms of mechanical strength, the total thickness of a preparation can be made to have a thickness of 1.0 mm or more to solve such problem of mechanical strength by properly selecting a thickness of the nonadhesive layer from the range of 2.5 to 0.1 mm. A preparation having the adhesive layer of such small thickness has a characteristic of giving no feeling of touchy disconfort when used, for instance, stuck to the oral cavity.

The slow-releasing preparation of the present invention can be prepared, for instance, according to the following method. Polymer powder which is used as an adhesive ingredient and a desired medicament together with other ingredients which are added as case may require are thoroughly mixed to obtain an intimate powdery mixture. This powder may also be made into slag and further into granule. A proper amount of thus obtained powder or granule is compressed with the punch, dice, and press to obtain an adhesive layer. Then a mixture of ingredients which is expected to form a nonadhesive layer is placed on the adhesive layer and again compressed to prepare a two-layer tablet with ease. At the time of pressing, if the latter pressing is effected with higher pressure than the former pressing, the separation of the nonadhesive layer from the adhesive layer hardly occurs, thus offering a higher yield rate in general. The pressure for each pressing may be decided by making a proper selection of balanced pressure. What is referred to as an intimate powdery mixture in the above means a state of mixture in which the respective ingredients contained in the preparation are mixed most uniformly and free from the slightest maldistribution.

As for the form of a slow-releasing preparation of the present invention, a tablet of two layers is preferable; however, other form, for instance, such as a granule comprising two layers is also preferable depending upon the place of administration.

As for the medicaments to be used by intimately mixed at least in either one of the adhesive layer and the nonadhesive layer of the preparation of the present invention, general or local therapeutic or preventive remedy and zoopharmaceutical, which are expected to obtain much more success in treatment by way of slow-releasing administration, may be mentioned. For concrete examples, they are analgesics and antiphlogistics such as acetaminophen, phenacetin, Aspirin, aminopyrine, sulpyrine, phenylbutazone, mefenamic acid, flufenamic acid, Ibufenac, Ibuprofen, indomethacin, colchicine, and Probenecid; antiinflammatory enzymes such as α-chymotrypsin; antiinflammatory steroids such as hydrocortisone, prednison, prednisolone, triamcinolone acetonide, dexamethasone, betaamethasone, etc.; antihistamines such as diphenhydramine hydrochloride, chlorpheniramine maleate, etc.; antibiotics or antimicrophytes such as tetracycline hydrochloride, leucomycin, fradiomycin, penicillin and its derivatives, cephalosporin derivatives, erythromycin, etc.; chemotherapeutics such as sulfathiazole, nitrofurazone; local anesthetics such as benzocaine, etc.; cardiac tonics such as digitalis, digoxin, etc.; vasodilators such as nitroglycerin, papaverine hydrochloride, etc.; antitussives and expectorants such as codeine phosphate, isoproterenol hydrochloride, etc.; oral antiseptics such as chlorhexidine hydrochloride, hexylresorcin, dequalinium chloride, cetylpyridinium chloride, ethacridine, etc.; drugs for the digestive organs such as pepstatin, azalene, phenovalin, vitamin U, etc.; enzymes such as lysozyme chloride, dextranase, etc.; hypoglycemics such as insulin, etc.; and other drugs including hemostats, sex hormones, hypotensives, sedatives, antitumor agents, antacids, etc. These drugs can be used either singly or as a mixture of two or more which are not therapheutically incompatible to each other. The amount of the drugs to be used in the preparation is the therapeutically effective amount required for the disease to which the preparation of the present invention is to be applied.

As for the lubricants which are used as occasion demands in the present invention, talc, stearic acid, stearate salts, and waxes may be mentioned. The binders include, for instance, starch, dextrin, tragacanth, gelatine, polyvinyl pyrrolidone, polyvinyl alcohol, hydroxypropyl cellulose, crystalline cellulose, hydroxypropylmethyl cellulose, ethyl cellulose, carboxymethyl cellulose, etc. The disintegrators include starch, crystalline cellulose, calcium carboxymethyl cellulose, etc. The excipients include starch, crystalline cellulose, dextrin, lactose, mannitol, sorbitol, calcium phosphoric acid anhydride, etc. The corrigents include citric acid, fumaric acid, tartaric acid, menthol citrus perfumes, etc.

The following examples illustrate the present invention in greater detail. Parts cited in the examples indicates parts by weight.

EXAMPLE 1

50 parts of polyacrylic copolymer (copolymer mainly comprising acrylic acid and allylsucrose, manufactured by B. F. Goodrich Chemical Co., Carbopol 934), 50 parts of hydroxypropyl cellulose and 0.5 part of magnesium stearate were measured as an adhesive layer matrix and 0.125 part of triamcinolone acetonide, anti-inflamatory drug, was measured as a medicament. The medicament was mixed with the matrix to obtain an intimate powder mixture for the adhesive layer use. On the other hand, 81 parts of lactose, 9 parts of hydroxypropyl cellulose, 10 parts of calcium carboxymethyl cellulose and 0.5 part of magnesium stearate were measured and mixed intimately to obtain a powder mixture for the nonexample before use.

With the use of the adhesive layer powder mixture as a lower layer material and the nonadhesive layer powder mixture as an upper layer material, two-layer tablets having a diameter of about 7 mm, with a lower layer weighing about 40 mg and having a thickness of about 1.1 mm and an upper layer weighing about 20 mg and having a thickness of about 0.4 mm, were obtained by use of an ordinary multilayer tablet machine. Following approximately the same procedures as above, two-layer tablets, which had the similar weight, thickness and content of the medicament, respectively comprising the combined components as shown in Table 1 mentioned below, were obtained.

TABLE 1

| No. | Adhesive layer | Nonadhesive layer |
|---|---|---|
| 1 | Polyacrylic acid (50) Methyl cellulose (50) | Lactose (95) Hydroxypropyl cellulose (5) |
| 2 | Hydroxypropylmethyl cellulose (100) | Crystalline cellulose (50) Starch (50) |
| 3 | Sodium polyacrylate (50) Hydroxyethyl cellylose (50) | Lactose (75) Starch (25) |
| 4 | Carboxymethyl cellulose (50) Hydroxypropyl cellulose (50) | Lactose (75), Starch (20), Hydroxypropyl cellulose (50) |
| 5 | Hydroxypropylmethyl cellulose (75) Hydroxypropyl starch starch (25) | Lactose (75) Starch (25) |
| 6 | Polyvinyl pyrrolidone (50) Carboxymethyl cellulose (50) | Hydroxypropyl starch (5) Chrystalline cellulose (85) Alminum silicate (10) |
| 7 | Gum arabi (30) Methyl cellulose (70) | Lactose (95) Hydroxypropyl cellulose (5) |
| 8 | Gelatine (40) Polyacrylic acid (50) Lactose (10) | Lactose (95) Hydroxypropyl cellulose (5) |
| 9 | Sodium carboxymethyl cellulose (40) Hydroxypropyl cellulose (50) Glucose (10) | Lactose (75) Starch (25) |
| 10 | Sodium alginate (40) Methyl cellulose (60) | Lactose (75) Starch (25) |
| 11 | Tragacanth gum (40) Hydroxypropyl-methyl cellulose (40) Methyl cellulose (20) | Lactose (75) Starch (25) |

The number in parentheses indicates parts.

All of these two-layer tables had enough adhesiveness to the mucous membrane of the oral cavity and their adhesive layers had a natone to swell gradually after the nonadhesive layer had dissolved or disintegrated.

EXAMPLE 2

This example is given to make it clear that the medicament is released slowly from the preparation of the present invention.

Predetermined amount of cellulose ether and polyacrylic acid shown in Table 2 below, a total of about 200 mg of a dye (amaranth), which corresponds to 4 mg per tablet, and 1 mg of magnesium stearate were mixed in a mixer. Discs having a weight of about 200 mg, a thickness of about 1.4 mm and a diameter of about 10.0 mm were press-formed from thus obtained intimate mixture. The discs were placed on agar gel at 37!C and the amount of the dye which was released into the agar with time was determined by measuring the absorbance at 520 m$\mu$ to obtain the release rate (%) of the dye. The results are shown in Table 2.

For comparison, discs were prepared in the same way as above using sucrose and lactose and subjected to the same test as above. The results are shown in Table 2.

chine. At this time, tablets under one group prepared with the adhesive layer powder mixture containing 0.125 part of dexamethasone were made to have an adhesive layer with varied weights of 40 mg, 80 mg, and 120 mg per tablet respectively and tablets under another group prepared with the adhesive layer powder mixture containing 0.33 part of dexamethasone were made to have an adhesive layer with varied weights of 15 mg and 10 mg per tablet respectively. The weight of a nonadhesive layer was 30 mg (about 0.5 mm thick) and the tablet diameter was 7 mm.

Tests were made with 30 panelists to see the adhesiveness of thus obtained two-layer tablets to the wet mucous surface (inside the lower lip of the mouth and the tip of the tongue) and the feeling of touchness

TABLE 2

| Component | Hydroxypropyl cellulose/ polyacrylic acid | | | | | Methyl cellulose/ polyacrylic acid | Hydroxyethyl cellulose/ polyacrylic acid | Hydroxypropyl- methyl cellulose/ polyacrylic acid | Sucrose | Lactose |
|---|---|---|---|---|---|---|---|---|---|---|
| Weight ratio | 90/10 | 75/25 | 65/35 | 50/50 | 25/75 | 85/15 | 85/15 | 85/15 | | |
| Standing time (hour) | | | | | | | | | | |
| 6 | 22.5 | 24.1 | 22.0 | 21.6 | 23.1 | 23.9 | 28.9 | 22.8 | 100 | 75.0 |
| 30 | 72.0 | 70.1 | 70.2 | 69.0 | 62.6 | 72.8 | 78.2 | 74.2 | — | 100 |
| 48 | 74.9 | 74.1 | 74.5 | 72.0 | 68.0 | 75.1 | 84.3 | 78.3 | — | — |
| 96 | 82.2 | 81.9 | 80.3 | 81.1 | 86.5 | 84.4 | — | 86.2 | — | — |

It is clearly seen from the results shown in the above that the releasing of the dye was constant and much slower in the preparations of the present invention than in the discs containing sucrose and lactose which are found with ordinary troches.

EXAMPLE 3

Two-layer tablets having the same components and combination as Example 1 were obtained, wherein 5 parts of cethylpyridinium chloride oral antiseptic was added to the nonadhesive layer in the place of triamcinolone acetonide which was used in Example 1 and the tablets were made to have a lower layer, or adhesive layer, having a weight of about 20 mg and a thickness of about 0.5 mm and an upper layer, or nonadhesive layer, having a weight of about 40 mg and a thickness of about 0.7 mm.

The two-layer tablets thus prepared also showed enough adhesiveness to the mucous membrane of the oral cavity and it was made clear that their nonadhesive layer had a nature to release the medicament as it dissolved in the oral cavity.

EXAMPLE 4

20 parts of polyacrylic acid, 80 parts of hydroxypropyl cellulose and 0.5 part of magnesium stearate were measured as an adhesive layer matrix and 0.125 part or 0.33 part of dexamethasone antiinflammatory drug was measured as a medicament to be contained in the adhesive layer. The medicament and the matrix were mixed intimately to obtain a powder mixture for adhesive layer use. On the other hand, 90 parts of lactose, 10 parts of hydroxypropyl starch, and 0.5 part of magnesium stearate were mixed uniformly to obtain a powder mixture for nonadhesive layer use.

With the use of the adhesive layer powder mixture as a lower layer material and the nonadhesive layer powder mixture as an upper layer material, two-layer tablets were obtained with an ordinary multilayer tablet macaused around the place where the tablets were adhered. The results are shown in Table 3, in which "excellent"! is given to cases where 30 to 25 panelists answered that the two-layer tablets showed satisfactory adhesiveness and caused no feeling of touchiness, "good" when 24 to 15 panelists answered to the same effect, and "fair" when 14 to 5 panelists were obtained.

TABLE 3

| Weight of adhesive layer (mg) | Thickness of adhesive layer (mm) | Adhesiveness | | Feeling of touchiness |
|---|---|---|---|---|
| | | Inside lower lip of mouth | Tip of tongue | |
| 120 | 2.9 | Excellent | Fair | Fair |
| 80 | 2.0 | Excellent | Fair | Good |
| 40 | 1.0 | Excellent | Good | Excellent |
| 15 | 0.4 | Excellent | Excellent | Excellent |
| 10 | 0.25 | Excellent | Excellent | Excellent |

It is seen from Table 3 that the slow-releasing preparation of this invention can be made to cause less feeling of touchiness by decreasing the thickness of the adhesive layer and also that the preparation can be made to have enough adhesiveness even to the place of vigorous movement such as the tip of the tongue.

EXAMPLE 5

Tests were made with 30 panelists to see the easiness of administration by adhering the tablets to the mucous membrane inside the lower lip of the mouth and the upper palate anterior and the occurrence of shifted adherence (displacement) to the facing mucous membrane (the gum) after the administration using the two-layer tablets prepared according to Example 1 and single-layer tablets composed solely of the lower layer of said two-layer tablets. Administration was effected by lightly placing the respective tablets on the mucous membrane inside the lower lip of the mouth with a pincette. To the upper palate anterior, each tablet was administered by carrying it on the tip of a clean finger and being pressed lightly. The results are shown in Table 4.

TABLE 4

|  | Frequency of failed administration/frequency of tests | | Shifting to facing mucous membrane |
| --- | --- | --- | --- |
|  | Inside lower lip of mouth | Upper palate anterior | Inside lower lip of mouth |
| Two-layer tablet (according to this invention) | 0/90 | 1/90 | 0/90 |
| Single-layer tablet (comparison) | 3/90 | 48/90 | 48/90 |

It is seen from Table 4 that the slow-releasing preparation (two-layer tablet) of the present invention is exceedingly superior to publicly known conventional single-layer tablet in handling to make administration much easier.

EXAMPLE 6

The hardness was compared between the two-layer tablets comprising an adhesive layer whose weight was 15 mg and a nonadhesive layer whose weight was 30 mg according to Example 4 and the single-layer tablets prepared solely with the lower layer corresponding to the adhesive layer of said two-layer tablets. The results are shown in Table 5.

TABLE 5

|  | Average hardness ± standard deviation |
| --- | --- |
| Two-layer tablet (according to this invention) | 3.5 ± 0.5 |
| Single-layer tablet (comparison) | 0.3 ± 0.1 |

It has been confirmed that the hardness of the tablets is improved by preparing them in the form of a two-layer tablet and no damage is caused to the tablets at the time of their manufacture, packaging, and handling. It has also been confirmed that the nonadhesive layer of the two-layer tablet dissolves or disintegrates gradually and thereafter both the two-layer tablet and the single-layer tablet shown in Table 5 have the similar degree of feeling of touchiness.

EXAMPLE 7

This example is given to show the adhesiveness of the adhesive layer of the slow-releasing preparation of this invention to the wet surface.

Discs, about 90 mg in weight, about 2 mm in thickness, and about 7 mm in diameter, were obtained by press-forming from respective mixtures mainly consisting of adhesive and swellable polymers as shown in Table 6. These discs were placed on a smooth surfaced wood block which was slightly moistened with water and one side of the disks was adhered to the wood block under a load of 100 g. A rubber sheet lined with a steel plate equipped with a hook was slightly moistened with water and placed on said fixed discs. A load of 100 g was exerted for 30 seconds to adhere the discs to the rubber sheet. Then the wood block was held upon a stand with the wood block above the rubber sheet. Water was filled between the wood block and the rubber sheet. A load was exerted on the hook attached to the rubber sheet to measure the load required for peeling off the rubber sheet from the discs to determine the adhesiveness of the discs under the wet condition. The results are shown in Table 6.

It is seen from Table 6 that the adhesive layer of the slow-releasing preparation of the present invention has enough adhesiveness to the wet surface.

TABLE 6

| NO. | Adhesive layer | Adhesiveness (g/cm$^2$) |
| --- | --- | --- |
| 1 | Polyacrylic acid (50) Methyl cellulose (50) | 600 |
| 2 | Hydroxypropylmethyl cellulose (100) | 750 |
| 3 | Sodium polyacrylate (50) Hydroxyethyl cellulose (50) | 450 |
| 4 | Carboxymethyl cellulose (50) Hydroxypropyl cellulose (50) | 300 |
| 5 | Hydroxypropylmethyl cellulose (75) Hydroxypropyl starch (25) | 450 |
| 6 | Polyvinyl pyrrolidone (50) Carboxymethyl cellulose (50) | 750 |
| 7 | Gum arabi (30) Methyl cellulose (70) | 250 |
| 8 | Gelatine (40) Polyacrylic acid (50) Lactose (10) | 200 |
| 9 | Sodium carboxymethyl cellulose (40) Hydroxypropyl cellulose (50) Glucose (10) | 150 |
| 10 | Sodium alginate (40) Methyl cellulose (60) | 200 |
| 11 | Tragacanth gum (40) Hydroxypropylmethyl cellulose (40) Methyl cellulose (20) | 600 |
| 12 | Hydroxypropyl cellulose (100) Alginic acid (80) | 300 |
| 13 | Lactose (20) | 50 |
| 14 | Methyl cellulose (100) | 150 |
| 15 | Carboxymethyl cellulose (100) | 150 |

INDUSTRIAL APPLICATION

The slow-releasing preparation offered by the present invention is a novel pharmaceutical preparation consisting of two layers, an adhesive layer and a nonadhesive layer, and displays an excellent efficacy not attained by any publicly known prior arts. It can be conveniently handled and securely adhered to a desired location of administration. As the thickness of its adhesive layer can be made very thin, it causes the smallest possible feeling of touchy irritancy while in use. The slow-releasing preparation of the present invention can be used for curing or preventing general or local diseases wherein the slow-releasing method is expected to have increased efficacy than the conventional methods, especially for the diseases in the body cavity such as oral, auricular, nasal, ophthalmic, urinary, genital and anal diseases, or can also be applied to the wet mucous surface resulting from operation, cut, and wound.

We claim:

1. A slow-releasing medical preparation to be administered by adhering to a wet mucous surface comprising an adhesive layer composed of a polymer which has the adhesiveness to a wet mucous surface and a property to swell upon moistening and a nonadhesive, either water soluble or disintegrable, layer which has no adhesiveness to a wet mucous surface and at least either one of said adhesive layer and nonadhesive layer is made to contain a medicament.

2. A slow-releasing medical preparation to be administered by adhering to a wet mucous surface according to claim 1, wherein a medicament is contained in the adhesive layer as an intimate mixture.

3. A slow-releasing medical preparation to be administered by adhering to a wet mucous surface according to claim 1, wherein the thickness of the adhesive layer is about 0.1 to 2.5 mm.

4. A slow-releasing medical preparation to be administered by adhering to a wet mucous surface according to claim 1, wherein the adhesive layer has the adhesiveness of about 40 g/cm$^2$ (adhesion area) or more.

5. A slow-releasing medical preparation to be administered by adhering to a wet mucous surface according to claim 1, wherein the preparation assumes the form of a tablet consisting of two layers.

6. A slow-releasing medical preparation to be administered by adhering to a wet mucous surface according to claim 1, wherein the polymer of the adhesive layer is at least one polymer selected from a group comprising acrylic acids or their pharmaceutically acceptable nontoxic salts, copolymers of acrylic acid or their pharmaceutically acceptable nontoxic salts, hydrophilic vinyl copolymers not copolymerized with acrylic acid as a main component, hydrophilic cellulose derivatives, polysaccharides or their derivatives and gelatine or collagen or their derivatives with improved swellability.

7. A slow-releasing medical preparation to be administered by adhering to a wet mucous surface according to claim 1, wherein the polymer of the adhesive layer is a mixture of cellulose ether and polyacrylic acid (or its salt) or copolymer of acrylic acid (or its salt).

8. A slow-releasing medical preparation to be administered by adhering to a wet mucous surface according to claim 1, wherein the nonadhesive layer comprises lactose or glucose or their mixture.

9. A slow-releasing medical preparation to be administered by adhering to a wet mucous surface according to claim 7, wherein the cellulose ether is methyl cellulose, hydroxypropyl cellulose, hydroxypropylmethyl cellulose or their mixture.

* * * * *